United States Patent [19]

MacLean et al.

[11] 3,979,666
[45] Sept. 7, 1976

[54] METHOD AND APPARATUS FOR EVALUATING PROPERTIES OF CARBON FIBERS USING CAPACITANCE SENSING

[75] Inventors: Alexander F. MacLean, Durham, N.H.; Ilmar L. Kalniv, Millington, N.J.

[73] Assignee: Celanese Corporation, New York, N.Y.

[22] Filed: Oct. 1, 1974

[21] Appl. No.: 511,008

Related U.S. Application Data

[62] Division of Ser. No. 326,711, Jan. 26, 1973, Pat. No. 3,864,626.

[52] U.S. Cl. .............................. 324/61 R; 324/30 B
[51] Int. Cl.² .......................................... G01R 27/26
[58] Field of Search .................. 324/61 R, 61 P, 71, 324/30 B; 117/201

[56] References Cited
UNITED STATES PATENTS

| | | | |
|---|---|---|---|
| 2,942,181 | 6/1960 | Edwards et al. | 324/61 R X |
| 2,966,628 | 12/1960 | Bosch | 324/61 R |
| 3,371,568 | 3/1968 | Felix | 324/61 R X |
| 3,778,705 | 12/1973 | Maltby | 324/61 R |

*Primary Examiner*—Stanley T. Krawczewicz

[57] ABSTRACT

A method and apparatus are provided for nondestructively evaluating physical properties of materials, and particularly semiconductive or electrically conductive fibers, e.g., carbonaceous fibrous materials containing at least about 90 per cent carbon by weight. The material is disposed in spaced relationship to a test electrode in an electrolytic solution and the physical property of the fiber is evaluated by evaluating the capacitance of the material. This capacitance evaluation may then be compared to the capacitance evaluation of a reference material having predetermined physical properties with the results of the comparison indicating the properties of the tested material. This indication may be utilized in the quality control of manufactured fibers by manual or automatic adjustment of the manufacturing process conditions. In fiber experimentation, this indication may be utilized to provide an evaluation of the effectiveness of an experimental process.

20 Claims, 3 Drawing Figures

METHOD AND APPARATUS FOR EVALUATING PROPERTIES OF CARBON FIBERS USING CAPACITANCE SENSING

This is a division of application Ser. No. 326,711, filed Jan. 26, 1973 now U.S. Pat. No. 3,864,626.

BACKGROUND OF THE INVENTION

The invention relates to a method and apparatus for evaluating physical properties of materials and, more particularly, for determining a physical property of a semi-conductive or electrically conductive material, such as a carbonaceous or other fiber, as a function of the relative capacitance of the material.

In the search for high performance materials, considerable interest has been focused upon carbon fibers. The term "carbon fibers" is used herein in its generic sense and includes graphite fibers as well as amorphous carbon fibers. Such carbonaceous fibers are electrically conductive and preferably contain at least about 90 per cent carbon by weight, and most preferably contain at least about 95 per cent carbon by weight. Graphite fibers exhibit a predominant x-ray diffraction pattern characteristic of graphite. Amorphous carbon fibers, on the other hand, are defined as fibers in which the bulk of the fiber weight can be attributed to carbon and which exhibit an essentially amorphous x-ray diffraction pattern. Graphite fibers generally have a higher Young's modulus than do amorphous carbon fibers and in addition are more highly electrically and thermally conductive.

Industrial high performance materials of the future are projected to make substantial utilization of fiber reinforced composites, and carbon fibers theoretically have among the best properties of any fiber for use as high strength reinforcement. Among these desirable properties are corrosion and high temperature resistance, low density, high tensile strength, and high modulus. Graphite is one of the very few known materials whose tensile strength increases with temperature. Uses for carbon fiber reinforced composites include recreational equipment such as golf club shafts, aerospace structural components, rocket motor casings, deep-submergence vessels, ablative materials for heat shields on re-entry vehicles, etc.

Carbon fibers, for optimum service, are required to meet predetermined criteria with respect to surface activity, bonding characteristics, and the like. For example, carbon fibers preferably exhibit a surface activity sufficient to form a strong bond with a resinous matrix material and thereby form a composite article exhibiting optimum physical properties, i.e., interlaminar shear strength.

In the past, the physical properties of carbon fibers have ordinarily been evaluated through the use of testing techniques which destroy or at least alter the fiber being tested and are extremely time consuming. For example, the bonding ability of a carbon fiber has been investigated by the evaluation of the horizontal short-beam shear strength of a test bar which incorporates the same within a matrix. This process is extremely laborious and time consuming, requires a skilled tester, and results in the destruction of the fiber. Likewise, the evaluation of a fiber surface area by the conventional BET (Brunauer-Emmet-Teller) method may require an average of about four hours of work by a skilled operator for each sample.

In addition to consuming great amounts of time of skilled personnel, these known testing methods are not readily adaptable to automation. Of course, the time requirements prevent the evaluation of fiber samples on a relatively continuing basis as the fiber is being manufactured. Moreover, the physical set-up required for these known tests makes these testing techniques impractical for use in relatively frequent quality control testing in a large scale carbon fiber manufacturing plant.

It is accordingly an object of the present invention to provide a novel method and apparatus for non-destructively evaluating a physical property of a material.

It is a more specific object of the present invention to provide a novel method and apparatus for non-destructively evaluating the surface characteristics of semi-conductive or electrically conductive fibers.

It is another object of the present invention to provide a novel method and apparatus for rapidly and accurately evaluating a physical property of a carbon fiber in relation to a corresponding physical property of a reference carbon fiber.

It is yet another object of the present invention to provide a novel method and apparatus for determining the relative capacitance of electrically conductive fibers to thereby provide an evaluation of relative physical characteristics of the fibers.

These and other objects and advantages are accomplished in accordance with the present invention as will become apparent to those skilled in the art from the following detailed description when read in conjunction with the attached drawings.

THE DRAWINGS

DETAILED DESCRIPTION

The materials evaluated may be semi-conductive or electrically conductive, and are preferably fibrous in nature. Such materials preferably possess a volume resistivity of less than 1,000,000 ohm cm. measured at 25°C., and most preferably a volume resistivity of less than 100,000 ohm cm. measured at 25°C. For instance, the fibrous materials may be carbonaceous and contain at least about 90 per cent carbon by weight, and most preferably contain at least about 95 per cent carbon by weight.

Figure 1:
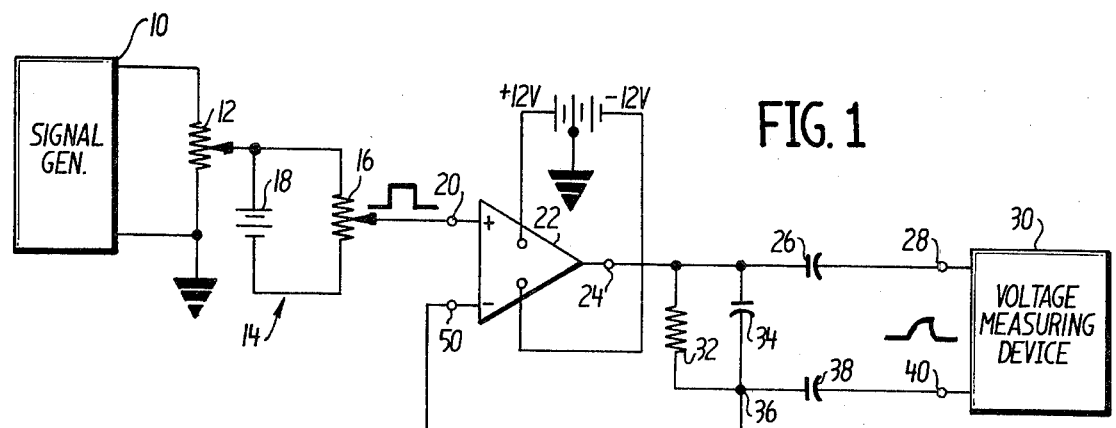
FIG. 1 is a schematic circuit diagram, partially in functional block form, of one embodiment of the apparatus of the present invention.

Referring to FIG. 1, an input signal, preferably a square wave, from a suitable conventional signal generator 10, such as the Hewlett Packard model 3300A function generator, may be applied to a potentiometer 12. A desired portion of the input signal may be selectively applied from the positionable arm of the potentiometer 12 to a d.c. biasing network generally indicated at 14, where for example, a potentiometer 16 connected in parallel with a d.c. source 18 has been illustrated. A pulse or a square wave signal from the generator 10 may be superimposed on a desired d.c. bias voltage and may be applied to the positive input terminal 20 of a suitable conventional operational amplifier 22. For example, the operational amplifier 22 may be a Philbrick/Nexus 1009 variable gain, differential d.c. amplifier biased as illustrated.

The output signal from the output terminal 24 of the amplifier 22 may be applied through a coupling capacitor 26 to an output terminal 28 and the output terminal 28 may be connected to one input terminal of a suitable conventional peak voltage indicating or measuring device 30 such as a Tektronix Type 536 differential input oscilloscope. The output terminal 24 of the operational amplifier 22 may also be connected through a parallel RC network including a resistor 32 and a reference capacitor 34 to a terminal 36, and the terminal 36 may be connected through a coupling capacitor 38 to a second output terminal 40. The output terminal 40 may be connected to a second input terminal of the voltage measuring device 30.

The terminal 36 also may be connected to a measuring electrode 42 of an electrolytic cell 44 of which a second measuring electrode 46 may be grounded. A reference electrode 48 of the electrolytic cell 44 may be connected to the negative input terminal 50 of the amplifier 22.

The electrolytic cell 44 also preferably includes an electrically non-conductive container or enclosure 52 filled with an aqueous strong electrolyte, e.g., one molar $LiClO_4$, $K_2CO_3$, NaOH or $HClO_4$ solution. The electrolyte may be an acid, a base, or a salt, as will be apparent to those skilled in the art. An electrolyte is preferably selected which has no substantial detrimental influence on the material undergoing testing. The molarity of the electrolyte may be varied widely so long as the resistance of the electrolyte does not become so high as to distort the signal being sensed, e.g., greater than about 100,000 ohms. The temperature of the electrolyte may be varied so long as the material being tested is not deleteriously influenced.

The electrodes 42, 46 and 48 may be immersed in the electrolyte, or at least in contact therewith, to provide a low resistance electrical path (on the order of a few thousand ohms) between the various electrodes of the cell. One of the measuring electrodes 42 and 46, for example the electrode 42, preferably is the counter-electrode and may be, for example, a platinum wire, and is usually negative with respect to the other measuring electrode 46, which is the electrode made of the test material, such as a carbon fiber to be tested.

The reference electrode 48 maintains a constant potential between the electrode 46 and the electrolyte in the container 52. A saturated calomel electrode may be utilized as the reference electrode 48 to accomplish this purpose.

Typical component values which may be utilized in the above described circuit for testing carbon fibers are as follows:

| Component | Value |
|---|---|
| Potentiometer 12 | 50 K ohms |
| Potentiometer 16 | 50 K ohms |
| Resistor 17 | 10 K ohms |
| Resistor 32 | 90 K ohms |
| Reference Capacitor 34 | 12 millifarads |
| Coupling Capacitors 26 and 38 | 1 microfarad |

In operation, a desired portion of the amplitude of the output signal from the signal generator 10 may be selected by adjusting the arm of a potentiometer 12 and this signal of selected amplitude may be superimposed on a desired d.c. level selected by adjusting the arm of the potentiometer 16. When the relative fiber capacitance of a graphite fiber is being tested, this signal may be, for example, a low frequency squarewave signal having a frequency of at least 10 pulses per minute, and preferably 10 and 100 pulses per minute. The amplitude of the signal is preferably at least 30 millivolts and is preferably between 30 and 50 millivolts. The d.c. bias upon which a squarewave signal is superimposed keeps the reference electrode 48 negative with respect to the test electrode 46 and may be, for example, sufficient to keep the reference electrode 48 at −0.1 volt with respect to the test electrode 46 when testing carbon fibers.

With continued reference to FIG. 1, the output signal from the amplifier 22 is applied across the parallel combination of the resistor 32 and the reference capacitor 34 in series with the electrolytic cell 44. The amplitude of the voltage developed across the reference capacitor 34 may be measured by the voltage measuring device 30 and this measured amplitude may then be utilized to compute the capacitance attributable to the electrolytic cell or capacitor 44 through the use of the following equation:

$$C = K \frac{(V_2)}{(V_1)} \quad (1)$$

where
C is the capacitance attributable to the electrolytic cell;
K is the capacitance of the reference capacitor 34;
$V_2$ is the peak amplitude of the output voltage between the terminals 28 and 40; and,
$V_1$ is the peak amplitude of the input signal applied to the terminal 20 of the amplifier 22.

It should be noted in connection with equation (1) that several constants have been ignored in obtaining the capacitance attributable to the test electrode 46 and that the resulting capacitance figure thus may not be an exact quantitative result. For example, the gain of the amplifier 22 and the effect of the reference electrode 48 may be ignored in obtaining the capacitance value C. However, the resulting capacitance value C attributable to, and thus related to, the capacitance of the only variable, i.e., the test electrode 46, may be utilized to evaluate relative properties of various fibers.

In this respect it should be noted that the spacing between the electrodes is maintained the same for a particular test run involving the testing of a group of fibers thereby eliminating any variables which might otherwise occur due to varying electrode spacing. Moreover, each fiber sample may be wetted by immersing the fiber in a bath containing a suitable wetting solution such as t-butanol. This wetting apparently eliminates or at least minimizes distortion of the double layer between the electrolyte and the fiber surface, the double layer apparently being responsible for the observed capacitance, as well as permits a complete access of the electrolyte to all the available surface of the test material.

The capacitance value C obtained for each test fiber may be divided by the weight W of that fiber for which the value C was obtained or by the length of the fiber where all of the fibers utilized as the test electrode 46 have a constant denier to thereby provide a "normalized" capacitance value. In this manner capacitance values attributable to each fiber relative to the capacitance value attributable to each of the other fibers tested (i.e., the relative fiber capacitance RFC of each fiber, which may be expressed in millifarads per gram) may be calculated by the following equation:

$$RFC = \frac{KV_2}{WV_1} = \frac{C}{W} \quad (2)$$

The relative fiber capacitance values RFC for a group of fibers may be compared and used for various purposes. For example, the RFC values may be used for quality control to determine the relative quality of fibers prepared in the same manner, or may be used to evaluate the effectiveness of various surface treatment techniques which are conducted subsequent to fiber preparation.

Alternatively, the relative fiber capacitance value RFC for a reference or standard fiber having known physical characteristics may be obtained and the relative fiber capacitance values may be utilized to evaluate certain physical characteristics of the test fibers relative to the reference fiber.

For example, the relative fiber capacitance of a carbon fiber, as measured in the manner described above, is related to the actual fiber surface area. Moreover, the introduction of chemically active groups on the surfaces of carbon fibers may be accomplished by a large increase in the relative fiber capacitance values obtained as described above.

Thus, with an indication of surface area and surface activity due to surface atoms or to functional atom groups deposited on the surface of the fiber, the relative fiber capacitance values may be utilized to provide an indication of the adhesion, catalytic activity, dye absorption and various other fiber properties relative to the corresponding properties of a standard or reference fiber or merely relative to each other. Moreover, if the specific surface areas S of the test fibers are known, a new relative measure of specific fiber surface activity, S.A., may be provided by dividing the RFC value by the specific surface area S, i.e., $$S.A. = \frac{RFC}{S} = \frac{KV_2}{WSV_1}. \quad (3)$$

Certain of these properties, in particular the adhesion properties of fibers, are particularly important when the fibers are fabricated into a fiber-resin composite. If the fibers adhere strongly to the resin matrix, the composite has certain desirable mechanical properties such as a high shear strength. The relative fiber capacitance values therefore become an extremely important tool in the quality control of fibers utilized in the production of a fiber-resin composite and in the quality control of the composites themselves. Additionally, these relative fiber capacitance values provide an extremely useful tool for rapidly evaluating the results of various methods utilized for the surface treatment of fibers.

In this respect, it should be noted that the measurement of actual fiber surface area by the conventional BET (Brunauer-Emmet-Teller) method requires an average of about four hours whereas the relative fiber capacitance measurement may be obtained in only a few minutes and may provide equally useful data. Likewise, as was mentioned previously, the relative fiber capacitance values provide a good indication of the attainable shear strength of a composite article made from the fibers for a given surface treatment and a given fiber type. This indication of shear strength through the use of relative fiber capacitance values again requires only a few minutes whereas many hours of expert effort may be required by the conventional horizontal short-beam shear strength test (ASTM D-2344) including the fabrication of a test bar, and its subsequent testing.

The significance of the use of RFC values as a quality control and experimentation tool may be more readily appreciated with reference to a specific example.

The conditions for achieving different shear strengths by surface treatment of carbon fibers were explored systematically using several lots of carbonaceous fibers exhibiting a predominantly graphitic carbon x-ray diffraction pattern and containing in excess of 95 per cent carbon by weight. A number of identical samples from one lot of a 25 end carbon yarn having a single filament Young's modulus of about 50,000,000 psi made in one continuous run were surface treated at temperatures ranging from 750 to 850°C. in various mixtures of oxygen and nitrogen under such conditions that the fiber surface was progressively more activated. The RFC values of samples before surface treatment and after surface treatment, together with the short-beam shear strength values obtained from composites which incorporate the surface treated samples, are given in the following Table I.

TABLE I

| Sample No. | RFC (millifarads/gram) | Short-Beam Shear Strength (psi) |
|---|---|---|
| 1* | 13 | not available |
| 2 | 18 | 3,200 |
| 3 | 62 | 5,500 |
| 4 | 55 | 12,900 |
| 5 | 66 | 12,900 |
| 6 | 71 | 12,200 |
| 7 | 71 | 12,200 |
| 8 | 15 | 2,900 |
| 9* | 6 | not available |

*Received no surface treatment in mixture of oxygen and nitrogen.

It can be seen from the above Table I that, with the exception of Sample No. 3, there is a good correlation between the RFC value and the short-beam shear strength value. Moreover, the RFC data show that the properties of the control yarns prior to surface treatment (Sample Nos. 1 and 9) may vary considerably even though they come from the same lot, i.e., from the end and the beginning of the lot, respectively.

Another set of identical carbon fiber samples take from a lot of carbonized yarn having a single filament Young's modulus of about 60,000,000 psi was treated at 780° to 820°C. with a mixture of oxygen-carbon dioxide-nitrogen gases under progressively more effective surface treatment conditions. The relationship between the RFC and the horizontal composite short-beam shear strength is shown in Table II.

TABLE II

| Sample No. | RFC (millifarads/gram) | Short-Beam Shear Strength (psi) | B.E.T. Surface Area (m²/gram) |
|---|---|---|---|
| 1* | 11.6 | 2600 | 0.38 |
| 2 | 24.0 | 6300 | 0.48 |
| 3 | 29.6 | 7700 | 0.53 |
| 4 | 40.0 | 10,200 | 0.60 |

TABLE II-continued

| Sample No. | RFC (millifarads/gram) | Short-Beam Shear Strength (psi) | B.E.T. Surface Area (m²/gram) |
|---|---|---|---|
| 5 | 35.6 | 10,400 | 0.58 |

*Sample treated with N₂ only, which should not affect the original surface.

It is seen that the RFC increases nearly linearly with increasing short-beam shear strength. Table II also shows that in this particular case, the increase in the RFC with increasing treatment is closely proportioned to the increase at the specific fiber surface area, i.e., the fiber surface activity per unit area remains unchanged.

In other cases, the surface activity may predominate and the RFC of a treated fiber may increase without a corresponding increase in the surface area.

Another illustrative example utilized a lot of high modulus, carbon fiber, having a single filament Young's modulus of about 80,000,000 psi. After a progressively more effective liquid phase surface treatment with a liquid acidic oxidant at temperatures ranging from 90° to 95°C., cooling down to room temperature and measuring the RFC of the treated fiber and the shear strength of unidirectional fiber-epoxy composites made with this fiber, the following data were obtained as reported in Table III.

TABLE III

| Sample No. | RFC (millifarads/gram) | Short-Beam Shear Strength (psi) |
|---|---|---|
| 1-L.* | 8 | 2800 |
| 2-L | 71 | 5700 |
| 3-L | 86 | 6900 |
| 4-L | 97 | 10,500 |

*Untreated.

It is seen that the liquid phase surface treatment greatly increases the fiber surface activity, whereas the composite short-beam shear strength in this and the previous instances reaches a limiting value, determined by the intrinsic fiber tensile strength, rather than the composite shear strength. As this limit the type of failure changes from fracture in shear (parallel to the long axis of the test specimen) to fracture in tension (perpendicular to the long axis of the test specimen). It is seen, therefore, that the RFC measurement is a much more sensitive indicator of the state of the treated or untreated fiber surface than any mechanical property of an interacting fiber-resin composite assembly.

It can readily be seen that the RFC data provide a rapid and reliable measure of the effectiveness of various surface treatments. The RFC data also indicate that there is probably a variance in the surface characteristics of carbon fibers produced in a single graphitization run. This variance may also exist over the span of a single surface treatment run. Thus, as a quality control tool, the RFC data may be utilized during a run to periodically or continuously monitor the relative surface capacitance along the length of the graphitized fiber and to adjust the treatment conditions accordingly.

Figure 2:
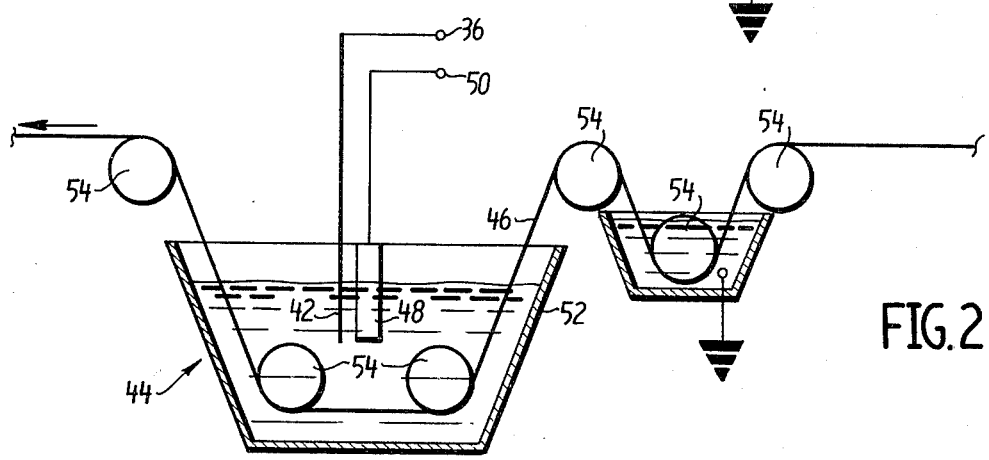
FIG. 2 is a schematic illustration in elevation of one embodiment of the apparatus of the present invention utilized in a continuous on-line fiber treating process.
Figure 3:
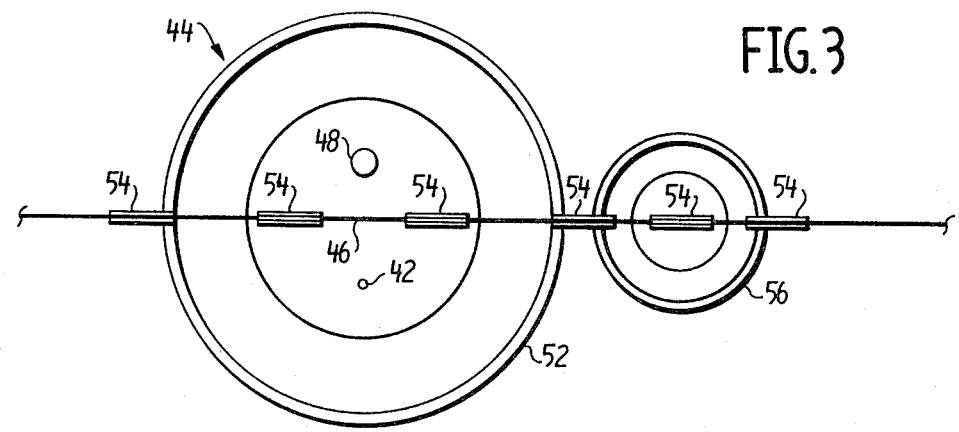
FIG. 3 is a schematic illustration in plan view of the apparatus of FIG. 2.

One way in which the surface capacitance (and thereby the physical properties) of continuous lengths of fibrous materials can be continuously monitored is illustrated in FIGS. 2 and 3.

Referring now to FIGS. 2 and 3 wherein the numerical designations previously utilized in connection with FIG. 1 have been utilized to designate like elements, the test electrode 46 comprising a continuous length of fibrous material may pass over a plurality of suitable electrically insulated guides 54 such as the illustrated rollers and may be directed through an electrolytic cell 44 such as the previously described electrolytic cell comprising the container 52 and the liquid electrolyte.

Electrical contact between the test electrode 46 and the external circuit previously described may be effected in any suitable conventional manner, for example, by directing the test electrode 46 through a liquid mercury bath 56 and making electrical contact between the mercury bath and the external circuit. The platinum counter electrode 42 and the saturated calomel reference electrode 48 may be positioned in the electrolyte on opposite sides of the test electrode 46 or in any other suitable location.

In operation, the fibrous material forming the test electrode 46, e.g., a continuous length of a carbonaceous fibrous material such as a yarn, tow, or other fiber assemblage, may be passed either continuously or intermittently through the electrolytic cell 44. The capacitance attributable to the test electrode may be monitored either continuously or periodically and converted to an RFC value.

The RFC values thus obtained then may be utilized, by the operator or through the use of an automatic servo system, to adjust the treatment conditions of the treatment process. For example, temperatures and/or gas constituency may be varied responsively to the RFC data to provide a continuous length of treated fibrous material having more consistent physical properties along the length thereof.

ADVANTAGES AND SCOPE OF THE INVENTION

It can be seen from the foregoing description that the present invention greatly facilitates the non-destructive evaluation of the physical properties of fibers. Fiber properties such as surface area and surface activity may be evaluated in a fraction of the time required by prior methods with a high degree of accuracy by a relatively unskilled operator.

In addition, the system of the present invention may be easily adapted to an automatic fiber manufacturing process for quality control and/or automatic process control. For example, fibers may be evaluated continuously and an alarm may be sounded or the process conditions may be altered in response to the evaluation.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A method for controlling the manufacturing process of a carbonaceous fibrous material containing at least about 90 percent carbon by weight comprising the steps of:

a. providing an electrolyte and a counter electrode in contact with the electrolyte;

b. disposing the carbonaceous fibrous material being manufactured in contact with the electrolyte at a predetermined distance from the counter electrode;

c. applying an electrical potential of known amplitude between the counter electrode and the carbonaceous fibrous material through a reference capacitor having a known value;

d. sensing the amplitude of an output potential across the reference capacitor;

e. evaluating a physical property of the carbonaceous fibrous material as a function of the sensed amplitude; and, f. controlling a process condition in response to the evaluation.

2. The method of claim 1 wherein said carbonaceous fibrous material exhibits a predominantly graphitic x-ray diffraction pattern.

3. The method of claim 1 including the further step of wetting the carbonaceous fibrous material in a wetting solution prior to disposing the carbonaceous fibrous material in contact with the electrolyte.

4. The method of claim 3 including the steps of:
a. disposing a reference electrode in contact with the electrolyte and spaced from the counter electrode and the carbonaceous fibrous material; and,
b. applying a predetermined bias potential between the reference electrode and the counter electrode.

5. The method of claim 4 wherein the electrical potential is applied between the carbonaceous fibrous material and the counter electrode periodically at a rate of at least 10 pulses per minute.

6. The method of claim 1 including:
a. dividing the sensed amplitude by a property of the carbonaceous fiber related to the fiber weight or size to obtain a normalized evaluation; and,
b. comparing the normalized evaluation with a normalized evaluation of a reference fiber to obtain a relative evaluation.

7. A method for controlling the manufacturing process of a carbonaceous fibrous material containing at least about 90 percent carbon by weight comprising the steps of:
a. disposing a predetermined portion of the carbonaceous fibrous material being manufactured in spaced relation to an electrode;
b. immersing the spaced carbonaceous fibrous material and electrode in an electrolytic solution to form an electrolytic cell having spaced electrodes;
c. sensing the capacitance between the carbonaceous fibrous material and the electrode in the electrolytic cell;
d. evaluating a physical property of the carbonaceous fibrous material as a function of the sensed capacitance; and,
e. controlling a process condition in response to the evaluation.

8. A method for controlling the manufacturing process of a carbonaceous fibrous material containing at least about 90 percent carbon by weight comprising the steps of:
a. providing an elongated electrode;
b. disposing the carbonaceous fibrous material being manufactured in a spaced relation to the electrode;
c. applying an unidirectional current pulse to either one of the fibrous material and the electrode;
d. sensing the current on the other of the carbonaceous fibrous material and the electrode;

e. evaluating the current sensed as the surface characteristic of the fibrous material; and, f. controlling a process condition in response to the evaluation.

9. The method of claim 8 wherein the carbonaceous fibrous material exhibits a predominantly graphitic x-ray diffraction pattern.

10. A method for controlling the manufacturing process of a continuous length of a carbonaceous fibrous material containing at least about 90 percent carbon by weight comprising the steps of:
a. providing an enclosure containing an electrolyte and a counter electrode in contact therewith;
b. passing the continuous length of carbonaceous fibrous material being manufactured as a continuous test electrode in contact with the electrolyte present in said enclosure at a predetermined distance from the counter electrode;
c. sensing the capacitance between the counter electrode and the fibrous material as the fibrous material passes through the electrolyte; and,
d. controlling a process condition in response to the sensed capacitance.

11. The method of claim 10 including the steps of:
a. disposing a reference electrode in contact with the electrolyte and spaced from the counter electrode and the carbonaceous fibrous material; and,
b. applying a predetermined bias potential between the reference electrode and the counter electrode.

12. The method of claim 11 including the further step of wetting the carbonaceous fibrous material in a wetting solution prior to disposing the fibrous material in contact with the electrolyte.

13. The method of claim 10 including the further step of wetting the carbonaceous fibrous material in a wetting solution prior to disposing the fibrous material in contact with the electrolyte.

14. Apparatus for controlling the manufacturing process of a fiber having an electrically conductive outer surface comprising:
a test electrode disposed in spaced relation to the fiber being evaluated;
an electrolyte intermediate the test electrode and the fiber and in contact with both the test electrode and the electrically conductive surface of the fiber being manufactured to thereby form an electrolytic cell;
means for sensing the capacitance of the electrolytic cell to thereby evaluate a physical property of the fiber; and,
controlling a process condition responsive to said sensing means.

15. The apparatus of claim 14 wherein said sensing means comprises:
a reference capacitor;
means for periodically applying an electrical potential through the reference capacitor to one of the test electrodes and the fiber;
means for sensing the potential across the reference capacitor; and,
means for providing an indication of the capacitance of the cell in response to the applied electrical potential and the sensed potential.

16. The apparatus of claim 15 including:
a reference electrode; and,
means for applying a bias potential between the reference electrode and the test electrode.

17. The apparatus of claim 15 wherein the fiber comprises a carbonaceous fibrous material containing at least 90 percent carbon by weight and means for moving the fibrous material through the electrolyte in contact therewith and in spaced relation to the test electrode.

18. The apparatus of claim 17 including a wetting solution for wetting the fibrous material prior to contacting the electrolyte.

19. Apparatus for controlling the manufacturing of a carbonaceous fibrous material containing at least about 90 percent carbon by weight comprising:
 a container provided with an electrolytic solution;
 a test electrode disposed within said container in contact with the electrolyte;
 means for disposing a carbonaceous fibrous material within said container in spaced relation to the test electrode at least a portion of said carbonaceous fibrous material being in contact with the electrolyte;
 a reference capacitor;
 means for periodically applying an electrical potential through said reference capacitor to one of said test electrodes and said carbonaceous fibrous material;
 means for sensing one of the potential developed between said test electrode and said carbonaceous fibrous material and the potential across said reference capacitor;
 means for evaluating a surface property of the carbonaceous fibrous material in response to the magnitudes of the applied potential and the sensed potential; and,
 means for controlling a process condition responsive to said evaluating means.

20. The apparatus of claim 19 including:
 a reference electrode disposed within said container in contact with the electrolyte; and,
 means for applying a bias potential between said reference electrode and said test electrode.

* * * * *